United States Patent [19]

Kaneko et al.

[11] Patent Number: 5,344,779
[45] Date of Patent: Sep. 6, 1994

[54] METHOD FOR PRODUCTION OF STANDARD OXIDE SAMPLE FOR X-RAY FLUORESCENCE SPECTROMETRY

[75] Inventors: Keiji Kaneko, Tsukuba; Masayuki Hirabayashi, Kashiwa; Hideo Ihara; Hiroko Kaneko, both of Tsukuba, all of Japan

[73] Assignee: Agency of Industrial Science & Technology, Ministry of International Trade & Industry, Tokyo, Japan

[21] Appl. No.: 35,211

[22] Filed: Mar. 22, 1993

[30] Foreign Application Priority Data

Jun. 26, 1992 [JP] Japan .................................. 4-192962

[51] Int. Cl.$^5$ ............................................ G01N 33/20
[52] U.S. Cl. ........................................ 436/19; 436/8; 252/408.1
[58] Field of Search ............... 436/8, 19, 127, 155; 252/408.1, 500

[56] References Cited

U.S. PATENT DOCUMENTS

| | | | |
|---|---|---|---|
| 3,015,544 | 1/1962 | Shaffer et al. | 436/19 |
| 3,951,854 | 4/1976 | Sias et al. | 436/19 |
| 3,983,077 | 9/1976 | Fuller et al. | 252/520 |
| 4,070,598 | 1/1978 | Deluca et al. | 313/487 |
| 4,715,988 | 12/1987 | Colin | 436/8 |
| 4,717,504 | 1/1988 | Hernicz | 252/408.1 |
| 4,813,580 | 3/1989 | DeAido, Jr. et al. | 222/590 |

OTHER PUBLICATIONS

Staats, G. "Synthetic macro reference samples for instrument calibration in inorganic bulk analysis" Proc. Chem. Conf. 42 rd 87-92, 1989.

Subrahmaniam, P. et al. "Titanium alloy standards for rapid analytical control" Trans. Indian Inst. Met., 39(4) 3925, 1986.

Yoshikazu Yamamoto et al, "Simultaneous determination of impurities in barium titanate by ICP-AES.", Dec. 2, 1985, Bunseki Kagaku, vol. 35 (1986), pp. 631–635.

Velmer A. Fassel, et al, "Simultaneous Determination of Wear Metals in Lubricating Oils by Inductively-Coupled Plasma Atomic Emission Spectrometry.", Mar. 1976, Analytical Chemistry, vol. 48, No. 3, pp. 516–519.

*Primary Examiner*—James C. Housel
*Assistant Examiner*—Rachel Heather Freed
*Attorney, Agent, or Firm*—Oblon, Spivak, McClelland, Maier & Neustadt

[57] ABSTRACT

A method for the production of a standard oxide sample for X-ray fluorescence analysis of an impurity element contained in an inorganic compound. The standard oxide sample is produced by accurately weighing a high-purity compound of the type of the main-component element of the inorganic compound, dissolving the weighed compound in an acid, adding an element of the type of the impurity element to be subjected to determination in a prescribed amount to the acid solution, evaporating the resultant solution to dryness, and heating the dry residue of evaporation.

6 Claims, 2 Drawing Sheets

METHOD FOR PRODUCTION OF STANDARD OXIDE SAMPLE FOR X-RAY FLUORESCENCE SPECTROMETRY

BACKGROUND OF THE INVENTION

1. Field of the Invention

This invention relates to a method for the production of a standard oxide sample for the determination of impurity elements contained in inorganic compounds such as raw material powders of refractory carbides, nitrides and borides, single crystals, oxides for the production of superconductors, and other industry grade oxides, by X-ray fluorescence spectrometry.

Such inorganic compounds contain minute amounts of various impurity elements such as chromium, manganese, iron, cobalt and nickel. In the production of a high-temperature superconductor from such a refractory inorganic compound, it is essential to be able to accurately determine the minute amount of impurity elements, in the compound.

2. Prior Art Statement

As observed in the process for determination of impurity elements in industry grade oxides, the determination of the impurity element content of a refractory inorganic compound has heretofore been performed by the method of chemically separating the inorganic compound into its main component element and its impurity elements (so as to reduce the effect of the large amount of main-component element) and then determining the impurity element content by ICP emission analysis or other spectroscopic analysis technique.

From the standpoint of the determination procedure, the chemical separation of the main element of the refractory inorganic compound from the minute amounts of impurity elements contained in the compound is extremely difficult, consumes much time, and is susceptible to experimental error.

In contrast, the nature of characteristic X-rays is such that even when the X-ray fluorescence is generated in the presence of large amounts of main-component elements, the characteristic X-rays of the impurity elements can be selectively determined within a range not affected by the main-component elements, with enhanced accuracy and reduced time consumption. Thus, X-ray fluorescence spectrometry is a suitable method for determination of minute amounts of impurity elements contained in the refractory inorganic compounds mentioned above.

In the method of X-ray fluorescence, the minute amounts of impurity elements have to be determined using calibration curves obtained using standard samples produced in advance. However, no one has ever produced the standard samples necessary for the determination of the impurity elements contained in the refractory inorganic compound by the method of X-ray fluorescence spectrometry.

The present inventors conducted a study on methods for effective solution of samples and conducted experiments using thermal decomposition curves, for the purpose of enabling the production of standard samples for determination of impurity elements in refractory inorganic compounds by the method of X-ray fluorescence spectrometry. This invention has been perfected as a result.

SUMMARY OF THE INVENTION

To be specific, this invention is directed to a method for the production of a standard oxide sample for the X-ray fluorescence spectrometry of impurity elements contained in an inorganic compound, which method is characterized by accurately weighing high-purity compounds of the main-component elements of an inorganic compound, dissolving the high-purity compound in an acid, adding prescribed amounts of impurity elements of the type to be determined to the acid solution, evaporating the resultant solution to dryness, and heating the dry residue obtained by evaporation under prescribed temperature conditions.

The above and other features of the invention will become apparent from the following description made with reference to the accompanying drawings.

DESCRIPTION OF THE PREFERRED EMBODIMENT

Figure 1:
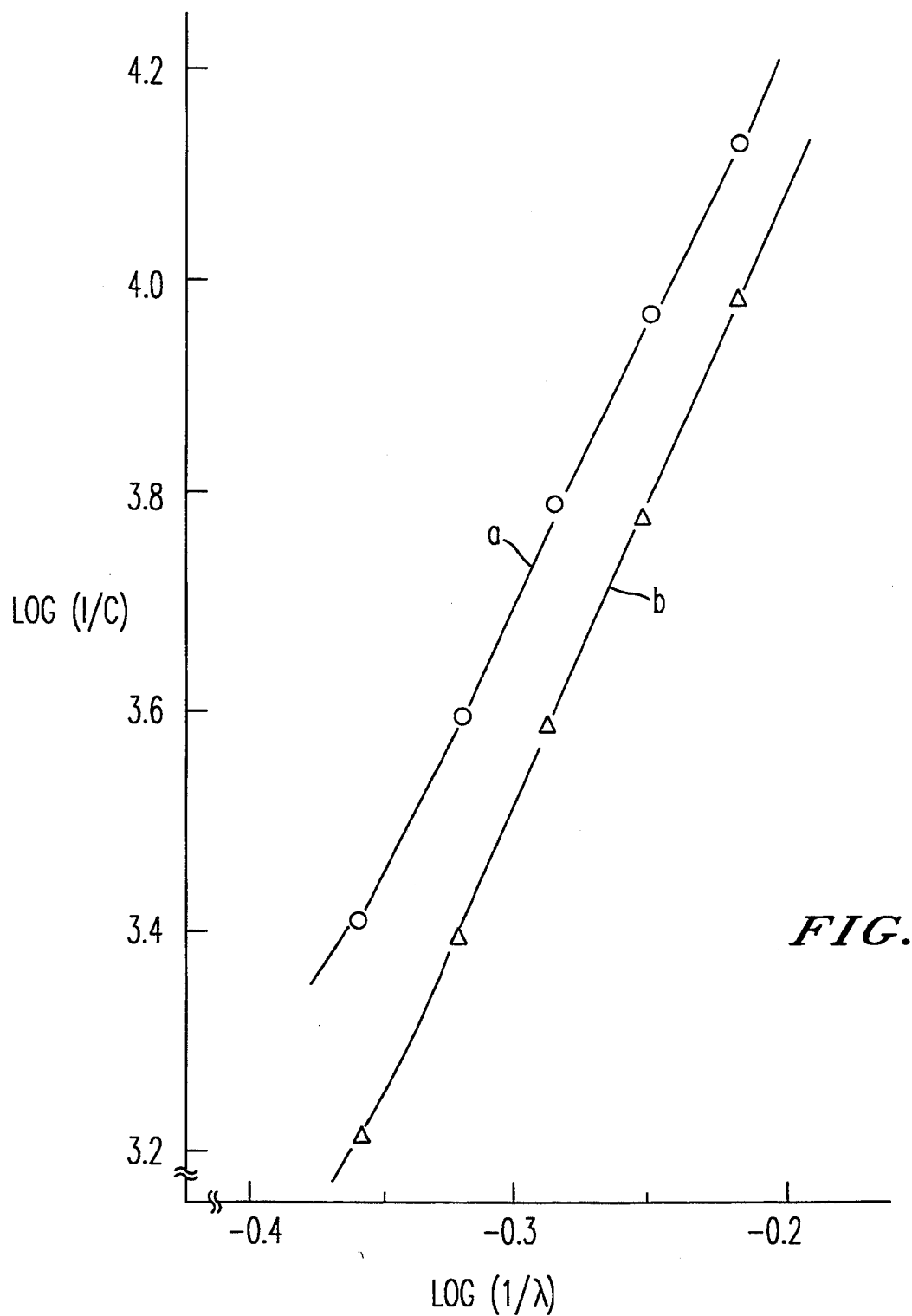
FIG. 1 is a graph showing the relation between Log (I/C) and Log (l/λ) obtained by using standard samples of titanium oxide and zirconium oxide.

The inorganic compounds to which the present invention can be effectively applied include raw material powders of refractory carbides, nitrides and borides, single crystals, oxides for manufacture of superconductors, and other industry grade oxide powders.

The high-purity compounds consisting of the main-component elements of these inorganic compounds and used as standard samples for the determination include metallic titanium, which is usable for the determination of impurity elements in titanium compounds, zirconium oxynitrate (chemical analysis grade), which is usable for the determination of impurity elements in zirconium compounds, yttrium oxide and lanthanum oxide (chemical analysis grade), which are usable for the determination of impurity elements in yttrium or lanthanum compounds, for example.

Now, the method for producing a standard sample from such a high-purity compound will be described.

First, the compound is dissolved in an acid (such as, for example, nitric acid, mixture of nitric acid and hydrochloric acid, or mixture of nitric acid and hydrogen fluoride). This solution is prepared in a plurality of portions so as to allow production of a plurality of samples containing the impurity elements in different concentrations. Then, the impurity element to be determined is added in different amounts to the portions to obtain standard samples containing the element in various concentrations.

Specifically, standard solutions which contain the impurity element in prescribed amounts are prepared. Then, these standard solutions are added to the portions mentioned above so as to give rise to mixed solutions containing the impurity element in the various volumes such as, for example, 0, 5, 10, 15 and 20 ml. These mixed solutions are subsequently required to be treated as described below so that the standard samples eventually obtained will contain the impurity element in concentrations in the range of from 1 to 2,000 ppm, for example.

Each of the solutions is placed in a crucible and evaporated to dryness. The resultant dry residue is placed in an electric furnace and heated, e.g., (from 100 to 600° C. at a rate of 100° C./2 hours, to obtain a plurality of standard samples. In the standard samples, the main-component element and the impurity elements are contained in the form of oxides.

For the purpose of simultaneously determining a plurality of elements such as chromium, manganese, iron, cobalt, nickel, copper, zinc, lead, zirconium, niobium, molybdenum, and tantalum, it suffices to produce standard oxide samples containing the oxides of these elements in accordance with the method described above.

Now, one example of the preparation of a calibration curve for the method of X-ray fluorescence spectrometry by the use of a plurality of standard oxide samples obtained as described above will be cited below.

Each of the plurality of standard oxide samples produced as described above is thoroughly crushed and mixed to obtain a powder 10 to 30 μm in particle diameter.

A prescribed amount of the powder is weighed out and compression molded to obtain a pellet. By the X-ray fluorescence technique, the characteristic X-ray of each element contained in the pellet is determined. The pellet may be in a suitable size. Its may be 20 mm (0.1 g) or 40 mm (4 g), for example.

After the X-ray analysis mentioned above, a calibration curve according to equation (1) or (2) below is prepared based on the results of the determination.

$$\text{Log } C = A \text{ Log } I + B \quad (1)$$

$$\text{Log } (I/C) = A (\text{Log } l/\lambda)^2 + B (\text{Log } l/\lambda) + D \quad (2)$$

wherein C stands for the concentration of an impurity element, I for the intensity of the characteristic X-ray, λ for the wavelength of characteristic X-ray, and A, B and D for constants.

Equation (1) represents the relationship between the concentration C of an element and the intensity I of the characteristic X-ray. The wavelength of the characteristic X-ray varies with the kind of element. When this function is used for the determination, therefore, it becomes necessary to prepare a calibration curve which is specifically proper for each of the elements being determined.

Equation (2) represents the relationship between the concentration C of an element and the wavelength λ and intensity I of characteristic X-ray. Thus, one calibration curve prepared for a standard oxide sample containing a plurality of elements permits simultaneous determination of the plurality of elements.

The calibration curves of the formula (1) and formula (2) can be prepared by the use of at least two standard oxide samples, i.e. a standard oxide sample containing no impurity element and a standard oxide sample containing impurity elements in prescribed amounts.

In summary then, the use of a standard oxide sample produced in accordance with this invention permits accurate determination of an impurity element contained in a concentration in the range of from 1 to 2,000 ppm in a refractory inorganic compound without requiring the step of chemical separation and even permits simultaneous determination of a plurality of impurity elements contained in an inorganic compound.

This invention allows production of a series of standard oxide samples with respect to virtually all ordinary elements. These standard oxide samples can be used semipermanently so long as the oxides are stable.

Now, this invention will be described below with reference to working examples.

EXAMPLE 1

2.9975 g of metallic titanium (99.9% or higher in purity) was dissolved in a mixture of hydrochloric acid and nitric acid. To the resultant solution, metal salts of chromium, manganese, iron, cobalt, nickel, copper, zinc, lead, zirconium, niobium, molybdenum, and tantalum were added respectively in the amounts of 624 ppm, 350 ppm, 335 ppm, 535 ppm, 106 ppm, 191 ppm, 196 ppm, 622 ppm, 294 ppm, 650 ppm, 336 ppm and 565 ppm as metals based on the amount of titanium. Then, the solution containing the added metal salts was evaporated to dryness. The dry residue was heated in an electric furnace up to 500° C. at a temperature increasing rate of 100° C./2 hours.

Part of the standard oxide sample prepared as described above was weighed out and compression molded into a pellet 20 mm in diameter. By the X-ray fluorescence spectrometry, the characteristic X-rays of the elements in the pellet were determined. The relationship between Log (I/C) and Log (l/λ obtained from the results of the test is shown in FIG. 1(a).

By the use of the calibration curve of FIG. 1(a) obtained using the standard oxide sample mentioned above, a raw material powder of commercially available titanium dioxide and a single crystal were subjected to determination of impurity element contents. The results are shown in Table 1.

Table 1 shows that the single crystal possessed very high purity as compared with the titanium dioxide.

EXAMPLE 2

Zirconium oxynitrate (chemical analysis grade) was weighed out in an amount calculated to form 5.500 g of an oxide thereof and dissolved in nitric acid. To the resultant solution, metal salts of chromium, manganese, iron, cobalt, nickel, copper, zinc, lead, niobium, molybdenum, and tantalum were respectively added in the amounts of 544 ppm, 288 ppm, 292 ppm, 463 ppm, 154 ppm, 166 ppm, 171 ppm, 542 ppm, 567 ppm, 293 ppm and 432 ppm as metals based on the amount of zirconium. Then, the solution containing the added metal salts was evaporated to dryness. The dry residue was heated in an electric furnace up to 600° C. at a temperature increasing rate of 100° C./2 hours to produce a standard oxide sample.

Part of the standard oxide sample was weighed out and then compression molded into a pellet 20 mm in diameter. By the X-ray fluorescence spectrometry, the characteristic X-rays of the elements in the pellet were determined. The relationship between Log (I/C) and Log (l/λ) obtained from the results of the test is shown in FIG. 1(b).

By the use of the calibration curve of FIG. 1(b) obtained using the standard oxide sample mentioned above, a raw material powder of commercially available zirconium carbide and single crystal were subjected to determination of impurity element contents. The results are shown in Table 1. Table 1 shows that the single crystal again possessed very high purity as compared with the raw material powder.

EXAMPLE 3

Yttrium oxide and lanthanum oxide (both chemical analysis grade) were weighed out in amounts calculated each to produce 4.000 g of an oxide thereof and separately dissolved in nitric acid. To each of the resultant solutions, metal salts of chromium, manganese, iron, cobalt, nickel, copper, zinc lead, zirconium, niobium, molybdenum, and tantalum were added respectively in the amounts of 624 ppm, 330 ppm, 335 ppm, 531 ppm, 176 ppm, 191 ppm, 196 ppm, 622 ppm, 274 ppm, 650 ppm, 330 ppm and 565 ppm as metals based on the amount of yttrium or lanthanum.

Then, the solutions containing the metal salts were evaporated to dryness. The dry residues were heated in an electric furnace up to 600° C. at a temperature increasing rate of 100° C./2 hours.

Part of each of the standard oxide samples produced as described above was weighed out and compression molded into a pellet 20 mm in diameter. By the X-ray fluorescence spectrometry, the characteristic X-rays of the elements in the pellet were determined. The relationship between Log (I/C) and Log (1/λ) obtained from the results of the determination are shown in FIG. 2(a) and (b).

Figure 2:
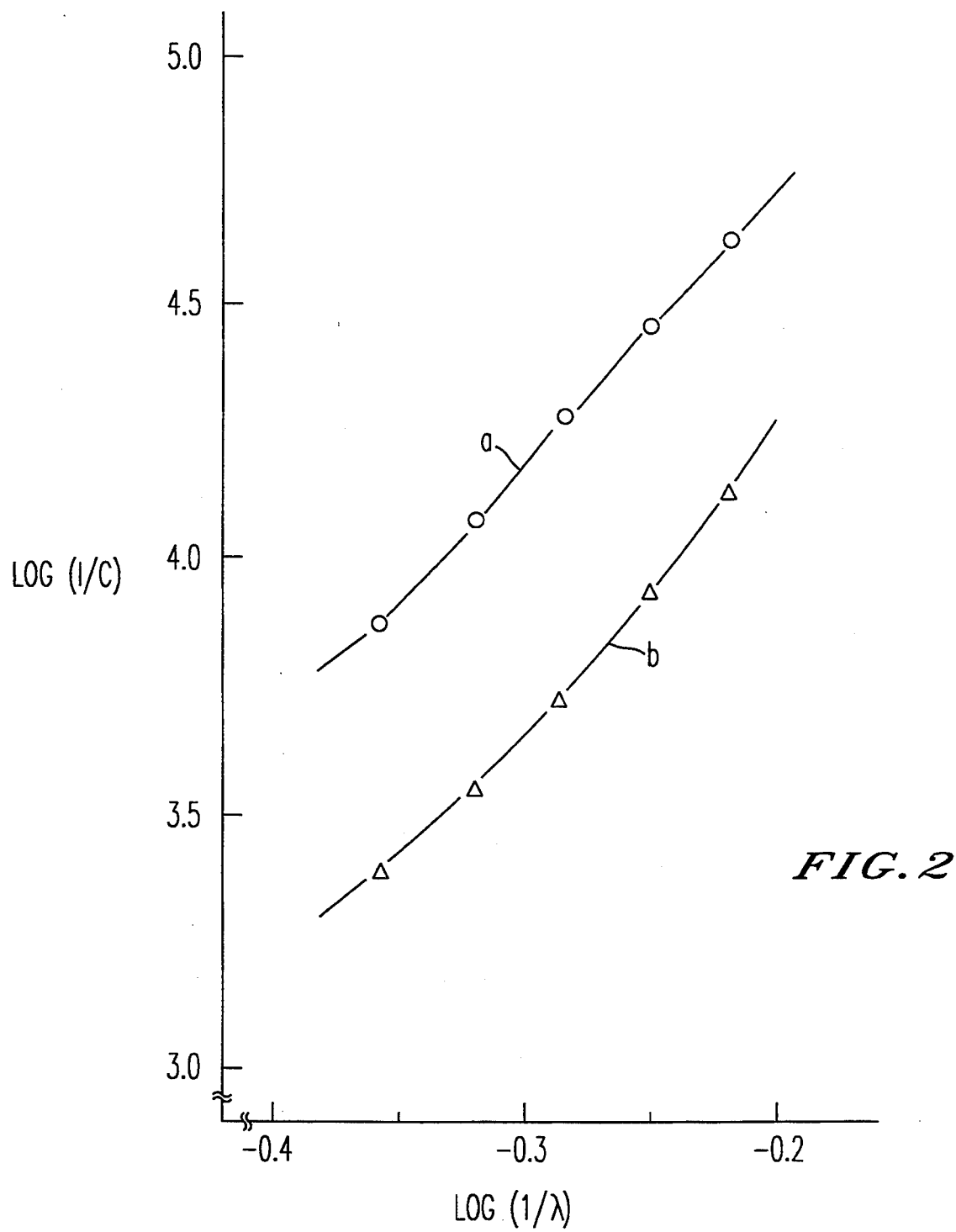
FIG. 2 is a graph showing the relation between Log (I/C) and Log (l/λ) obtained by using standard samples of yttrium oxide and lanthanum oxide.

By the use of the calibration curves of FIG. 2(a) and (b), raw material powders of yttrium hexaboride and lanthanum hexaboride and commercially available yttrium oxide and lanthanum oxide were subjected to determination of contents of impurity element. The results were as shown in Table 1 below.

TABLE 1

| | Chromium | Manganese | Iron | Cobalt | Nickel |
|---|---|---|---|---|---|
| Titanium diboride (powder) | 790 | 7 | 722 | 1500 | 74 |
| Titanium diboride (crystal) | 128 | 5 | 246 | 16 | 16 |
| Zirconium carbide (powder) | 265 | 35 | 473 | 98 | 82 |
| Zirconium carbide (crystal) | 177 | 30 | 254 | trace | 20 |
| Yttrium hexaboride (powder) | 771 | 5 | 1861 | 49 | 2773 |
| Lanthanum hexaboride (powder) | 91 | 5 | 1398 | 33 | 129 |
| Yttrium oxide (powder) | <10 | <10 | 16 | <10 | <10 |
| Lanthanum oxide (powder) | <10 | <10 | 20 | <10 | <10 |

TABLE 1-continued

What is claimed is:

1. A method for producing a standard oxide sample for use in measuring the content of a known impurity element in an organic compound by X-ray fluorescence analysis, said method comprising the steps of:
   a. dissolving said inorganic compound in nitric acid, nitric acid and hydrochloric acid, or nitric acid and hydrofluoric acid to obtain an acid solution thereof;
   b. adding said known impurity element to said acid solution in a concentration in the range of from 1 to 2,000 ppm based on the concentration of said inorganic compound to obtain a mixed solution wherein said known impurity has been dissolved in the acid;
   c. evaporating said mixed solution to dryness to obtain a dry residue of evaporation; and
   d. heating said dry residue of evaporation up to 600° C. to obtain said standard oxide sample containing said inorganic compound and said impurity.

2. The method according to claim 1, wherein said heating in step d. is from 100° to 600° C. at a rate of 100° C./2 hours.

3. The method according to claim 1, wherein said known impurity element added to said acid solution comprises at least two elements.

4. The method according to claim 1, wherein said inorganic compound is one member selected from the group consisting of refractory carbides, nitrides, borides and oxides.

5. The method according to claim 1 wherein said acid solution obtained in step a. is divided before step b. into a plurality of acid solutions, said known impurity element is added to said plurality of acid solutions in different concentrations, each in the range of from 1 to 2,000 ppm based on the concentration of the inorganic compound, to obtain a plurality of mixed solutions in step b. and a plurality of dry residue in step c., thereby obtaining a plurality of standard oxide samples containing different amounts of impurity elements, respectively.

6. The method according to claim 1, wherein said impurity element is at least one member selected from the group consisting of chromium, manganese, iron, cobalt, nickel copper, zinc, lead, zirconium, niobium, molybdenum and tantalum.

* * * * *